(12) United States Patent
Li et al.

(10) Patent No.: US 7,515,682 B2
(45) Date of Patent: Apr. 7, 2009

(54) METHOD AND SYSTEM TO GENERATE OBJECT IMAGE SLICES

(75) Inventors: Baojun Li, Waukesha, WI (US); Stephen W. Metz, Greenfield, WI (US); Jiang Hsieh, Brookfield, WI (US); Yogesh Srinivas, Hartland, WI (US); Xianfeng Ni, Merton, WI (US); Tabb Patz, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 136 days.

(21) Appl. No.: 11/345,918

(22) Filed: Feb. 2, 2006

(65) Prior Publication Data

US 2007/0183564 A1 Aug. 9, 2007

(51) Int. Cl.
*A61B 6/03* (2006.01)
(52) U.S. Cl. .................... 378/22; 378/210
(58) Field of Classification Search ............. 378/22, 378/210
See application file for complete search history.

(56) References Cited

U.S. PATENT DOCUMENTS

| | | | | |
|---|---|---|---|---|
| 4,216,526 | A * | 8/1980 | Karwowski | 378/4 |
| 4,903,204 | A * | 2/1990 | Dobbins, III | 382/255 |
| 6,196,715 | B1 * | 3/2001 | Nambu et al. | 378/197 |
| 6,529,575 | B1 * | 3/2003 | Hsieh | 378/4 |
| 6,885,764 | B2 * | 4/2005 | Wang et al. | 382/131 |
| 2002/0080921 | A1 * | 6/2002 | Smith et al. | 378/189 |
| 2002/0141532 | A1 * | 10/2002 | Koppe et al. | 378/21 |
| 2003/0007598 | A1 * | 1/2003 | Wang et al. | 378/37 |
| 2003/0210254 | A1 * | 11/2003 | Doan et al. | 345/661 |
| 2003/0212327 | A1 * | 11/2003 | Wang et al. | 600/437 |
| 2005/0002550 | A1 * | 1/2005 | Jabri et al. | 382/131 |
| 2005/0113681 | A1 * | 5/2005 | DeFreitas et al. | 600/426 |
| 2005/0135555 | A1 * | 6/2005 | Claus et al. | 378/19 |
| 2006/0029285 | A1 * | 2/2006 | Hein et al. | 382/260 |
| 2006/0098855 | A1 * | 5/2006 | Gkanatsios et al. | 382/128 |

(Continued)

FOREIGN PATENT DOCUMENTS

WO WO02/43801 * 6/2002

OTHER PUBLICATIONS

Li et al., The impact of acquisition angular range on the z-resolution of radiographic tomosynthesis, Jun. 2004, International Congress Series, vol. 1268, pp. 13-18, Proceedings of the 18th International Congress and Exposition—CARS 2004—Computer Assisted Radiography and Surgery.*

(Continued)

*Primary Examiner*—Edward J Glick
*Assistant Examiner*—John M Corbett
(74) *Attorney, Agent, or Firm*—Cantor Colburn LLP

(57) ABSTRACT

A method for creating a variable slice thickness for displaying an imaged object is disclosed. The method includes acquiring a plurality of projection images from a plurality of different projection angles within a defined sweep angle, reconstructing a plurality of object images from the plurality of projection images, each object image having a first slice thickness, and applying a function rule to combine images, whole images or portions thereof or attributes thereof, of the plurality of projection images, of the plurality of object images, or of both, thereby providing for the display of the object utilizing a second slice thickness that varies from the first slice thickness.

9 Claims, 7 Drawing Sheets

U.S. PATENT DOCUMENTS

2006/0153434 A1* 7/2006 Wang .................. 382/128

OTHER PUBLICATIONS

Al-Raoush, Extraction of Physically-Realistic Pore Network Properties from Three-Dimensional Synchrotron Microtomography Images of Unconsolidated Porous Media, Dec. 2002, PhD. Dissertation, Louisiana State University and Agricultural & Mechanical College, pp. 39-40.*

Hsieh, Computed Tomography: Principles, Designs, Artifacts, and Recent Advances, 2003, ISBN 0-8194-4425-1, pp. 265-269.*

Hu, Hui et al., "The effect of helical pitch and beam collimation on the lesion contrast and slice profile in helical CT imaging", Medical Phys. 23, pp. 1943-1954, 1996.

* cited by examiner

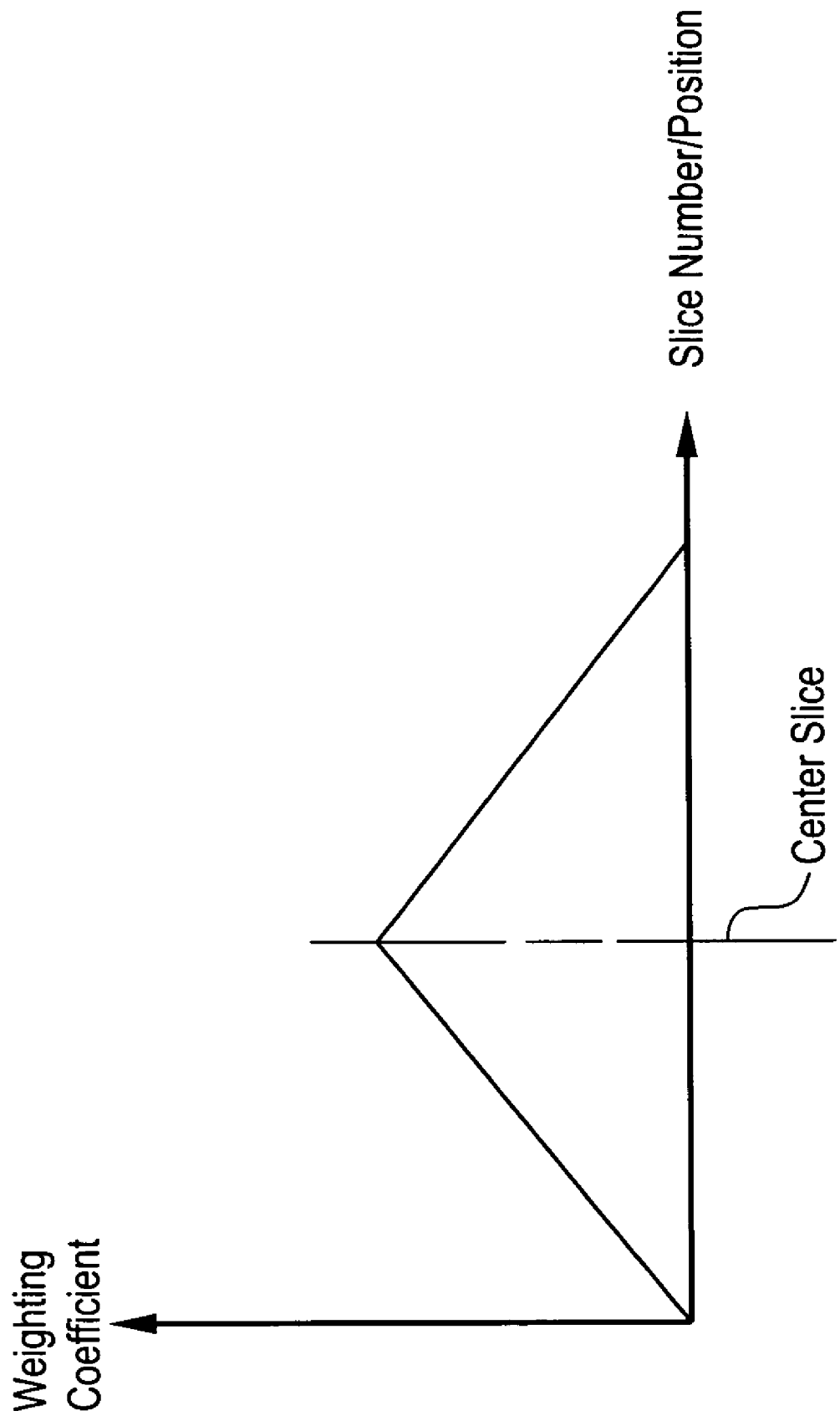

FIG. 6

Tomo Slices

To adjust default slice parameters; first select the receptor/anatomy/view/size combination.

Receptor: Wall Stand
Anatomy: Chest
View: postero-anterior
Patient Size: Medium Adult Start Height (mm) — 301
20 — 420

End Height (mm) — 301
270 — 421

Thickness (mm) — 306
5 — 423

Overlap (mm) — 311
25 — 422 # of slices: 63

Save    Save to Multiple    Close

419

US 7,515,682 B2

METHOD AND SYSTEM TO GENERATE OBJECT IMAGE SLICES

BACKGROUND OF THE INVENTION

The present disclosure relates generally to medical imaging, and particularly to the generation of object image slices.

Conventional (projection) X-ray imaging does not allow for viewing of detailed cross-sections of tissue structures at a predetermined depth. Tomosynthesis is an advanced application in X-ray radiographic imaging that allows retrospective reconstruction of an arbitrary number of tomographic planes of anatomy from a set of low-dose projection images acquired during a defined translation of an x-ray source, and provides for depth information relating to the projection images. The use of a digital flat panel, which may measure 40 centimeters (cm)×40 cm for example, allows large amounts of data to be collected with each exposure. The depth information carried by these tomographic planes is unavailable in conventional (projection) x-ray imaging.

With the introduction of tomosynthesis, it is possible to encode the depth information of the overlapping/underlying anatomical structures with the images. A minimum slice thickness (which is also referred to as a nominal slice thickness) of tomosynthetic image slices is determined primarily by a sweep angle of an x-ray source. Nominal slice thickness is usually defined by the full-width-half-maxima (FWHM) of the slice sensitivity profile (SSP), because the slice orientation is perpendicular to the x-ray detector panel. Although the nominal slice thickness may provide the maximum z-resolving power, thicker slices may provide practical benefit in many clinical settings.

Accordingly, the art of tomosynthesis imaging may be advanced by providing a method and system that is capable of generating and managing image slices of variable thickness.

BRIEF DESCRIPTION OF THE INVENTION

An embodiment of the invention includes a method for creating a variable slice thickness for displaying an imaged object. The method includes acquiring a plurality of projection images from a plurality of different projection angles within a defined sweep angle, reconstructing a plurality of object images from the plurality of projection images, each object image having a first slice thickness, and applying a function rule to combine images, whole images or portions thereof or attributes thereof, of the plurality of projection images, of the plurality of object images, or of both, thereby providing for the display of the object utilizing a second slice thickness that varies from the first slice thickness Another embodiment of the invention includes a user interface for displaying an imaged object, the imaged object having associated therewith a plurality of reconstructed object images each having a first slice thickness, the reconstructed object images having been reconstructed from a plurality of projection images. The user interface includes means for a user to select a function rule or a function rule parameter, means for applying the function rule or function rule parameter to combine images, thereby providing for the display of the object utilizing a second slice thickness that varies from the first slice thickness, and means for displaying a portion of the object at the second slice thickness. The function rule may combine whole images or portions thereof or attributes thereof, of the plurality of projection images, of the plurality of object images, or of both.

Another embodiment of the invention includes a system for imaging an object. The system includes an image detector, an imaging source capable of angular movement relative to the object, and a processing device in signal communication with the image detector and the imaging source. The imaging source is disposed to direct imaging radiation toward the image detector. In response to movement of the imaging source, a plurality of projection images from a plurality of different projection angles within a defined sweep angle is acquired at the image detector. The processing device is configured to reconstruct a plurality of object images from the plurality of projection images, each object image having a first slice thickness. The processing device is also configured to apply a function rule to combine images, whole images or portions thereof or attributes thereof, of the plurality of projection images, of the plurality of object images, or of both, thereby providing for display of the object utilizing a second slice thickness that varies from the first slice thickness.

BRIEF DESCRIPTION OF THE DRAWINGS

Referring to the exemplary drawings wherein like elements are numbered alike in the accompanying Figures:

FIG. 4 depicts a graph illustrating an exemplary weighting coefficient function in accordance with embodiments of the invention;

FIG. 6 depicts an exemplary embodiment of a dialog window to input image parameters in accordance with embodiments of the invention.

DETAILED DESCRIPTION OF THE INVENTION

An embodiment of the invention provides a radiologist with an interface to take advantage of flexibility to tailor tomosynthesis image slice thickness to best suit the diagnostic requirements of an application. Although a minimum (nominal) image slice thickness may provide maximum resolution within a direction of slice thickness, thicker slices may provide practical benefit in many clinical settings.

First, there are a number of clinical applications that favor thicker slices. For example, to diagnose interstitial diseases, the slice thickness of at least 1 cm may be preferred because vessel continuation is much better visualized. Another example is mammography, where the slice thickness of about 1 cm is advantageous to diagnose a presence of clustered micro calcifications. Second, image noise and artifacts are reduced during the forming of thicker slices. This is because of improved data consistency with thicker slices relative to thinner slices. In certain clinical applications, this reduction of image noise and artifacts is more valuable than the loss of local contrast and image sharpness that may accompany thicker image slices. Third, thicker slices may improve radiologist productivity. Clinical feedback has repeatedly emphasized that the large amount of images generated by tomosynthesis may have a significant impact on radiologist productivity and financial considerations.

For all of the above reasons, it is advantageous to create images of variable slice thickness via the combination of thin image slices into thicker image slices. The optimum slice thickness is dependent upon the diagnostic application and user preference, including trade-offs between coverage, slice thickness, and artifacts. An embodiment of the invention will allow a user to select the desired slice thickness based on the application and his/her preference.

Figure 1:
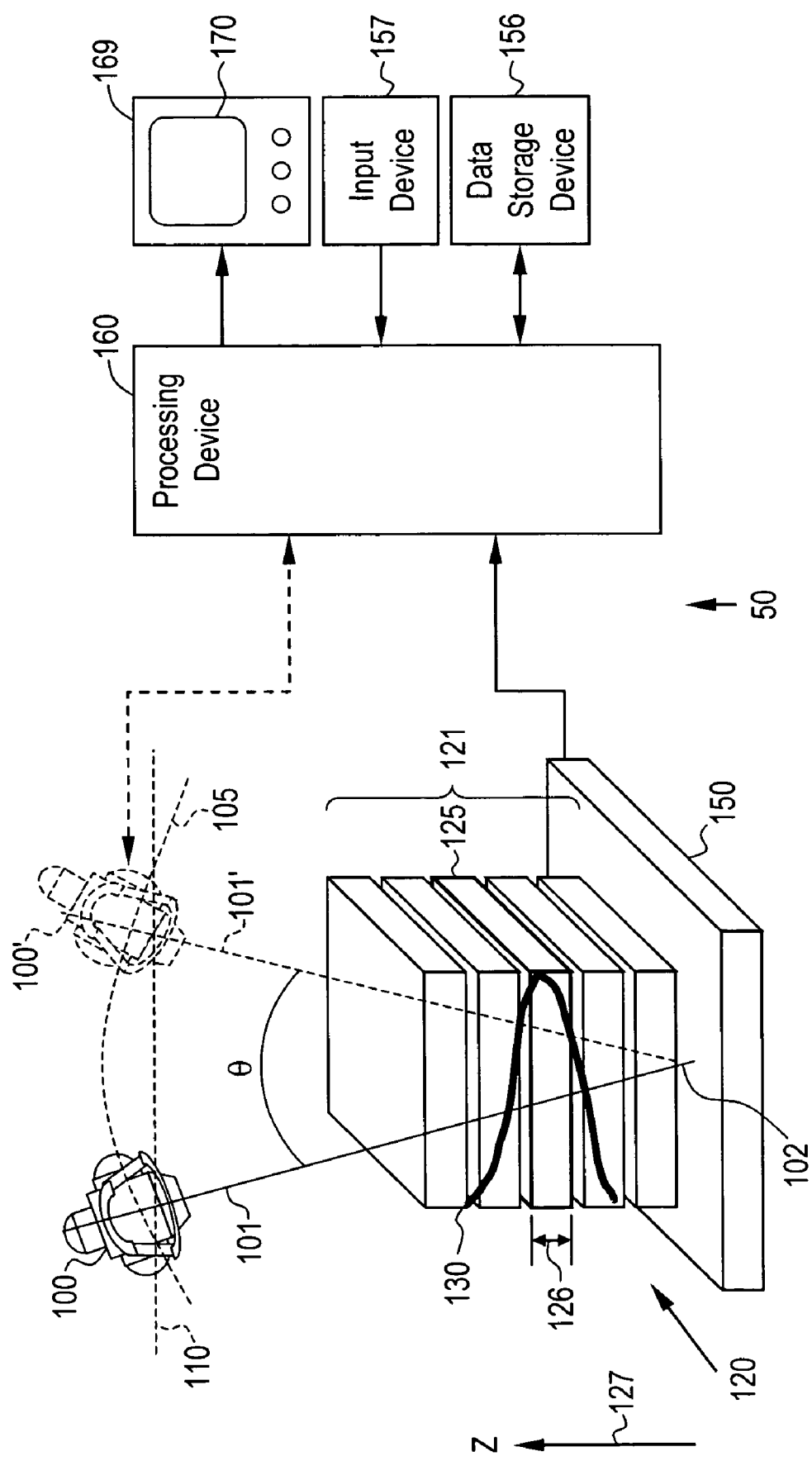
FIG. 1 depicts an exemplary block schematic tomosynthesis system in accordance with an embodiment of the invention.

Referring to FIG. 1, a schematic of an exemplary embodiment of a tomosynthesis system 50 is depicted. An x-ray source (also herein referred to as an imaging source) 100, projects an x-ray beam (also herein referred to as imaging radiation) 101, which is directed through an imaging object 120, such as a portion of human anatomy for example, toward a panel detector (also herein referred to as an image detector) 150, which is typically stationary and in an embodiment is two-dimensional. As the x-ray source 100 translates along either a defined arc trajectory 105 or a defined linear trajectory 110 from a first position (depicted by the disposition of x-ray source 100 in FIG. 1) to a second position (depicted by the disposition of x-ray source 100' in FIG. 1), the x-ray beam 101 travels through the imaging object 120. As the x-ray beam 101 passes through the imaging object 120, components of varying densities within the imaging object 120 provide for differential x-ray attenuation. An attenuated x-ray Beam 102 is received by the panel detector 150, which produces an electrical signal responsive to the intensity of the attenuated x-ray beam 102.

A processing device 160 communicates with the x-ray source 100 to provide power and timing signals. The processing device 160 is also in communication with a motor (not depicted in FIG. 1) to drive the translation of the x-ray source 100, the panel detector 150 to receive the electrical signal data for subsequent processing, a data storage device 156, an input device 157, and an output device 169. The processing device 160 reconstructs the electrical signal data, which represents a plurality of projection images, from the panel detector 150 into a plurality of individual image slices 125 of the imaging object 120. As used herein, reference in general to image slices will be to one of a group of image slices 121, as depicted in FIG. 1. Each image slice 121 represents a 3-D slice containing depth data, including relative positions and sizes of internal components with varying densities. Each image slice 121 has a depth-of-view in a z-direction 127 defined by a minimum (also herein referred to as a nominal or first) slice thickness 126, which will be described further below. The processing device 160 stores the image slices 121 in the data storage device 156 and displays the data signals as an image via the output device 169. In accordance with an exemplary embodiment, the image slices 121 are each individually viewable via a display screen 170 of the output device 169.

As the x-ray source 100 translates through a sweep angle θ from the first position of the x-ray source 100 to the second position of the x-ray source 100', a plurality of radiographic projection images are acquired by the panel detector 150 from a plurality of projection angles within the defined sweep angle θ. The sweep angle θ determines a slice sensitivity profile 130 and the nominal slice thickness 126. While an embodiment of the invention has been described employing the stationary flat panel detector 150, it will be appreciated that the scope of the invention is not so limited, and that the invention also applies to tomosynthesis systems 50 utilizing a panel detector which may have alternate shapes, such as a concave profile for example, and may also be capable of movement.

Figure 2:
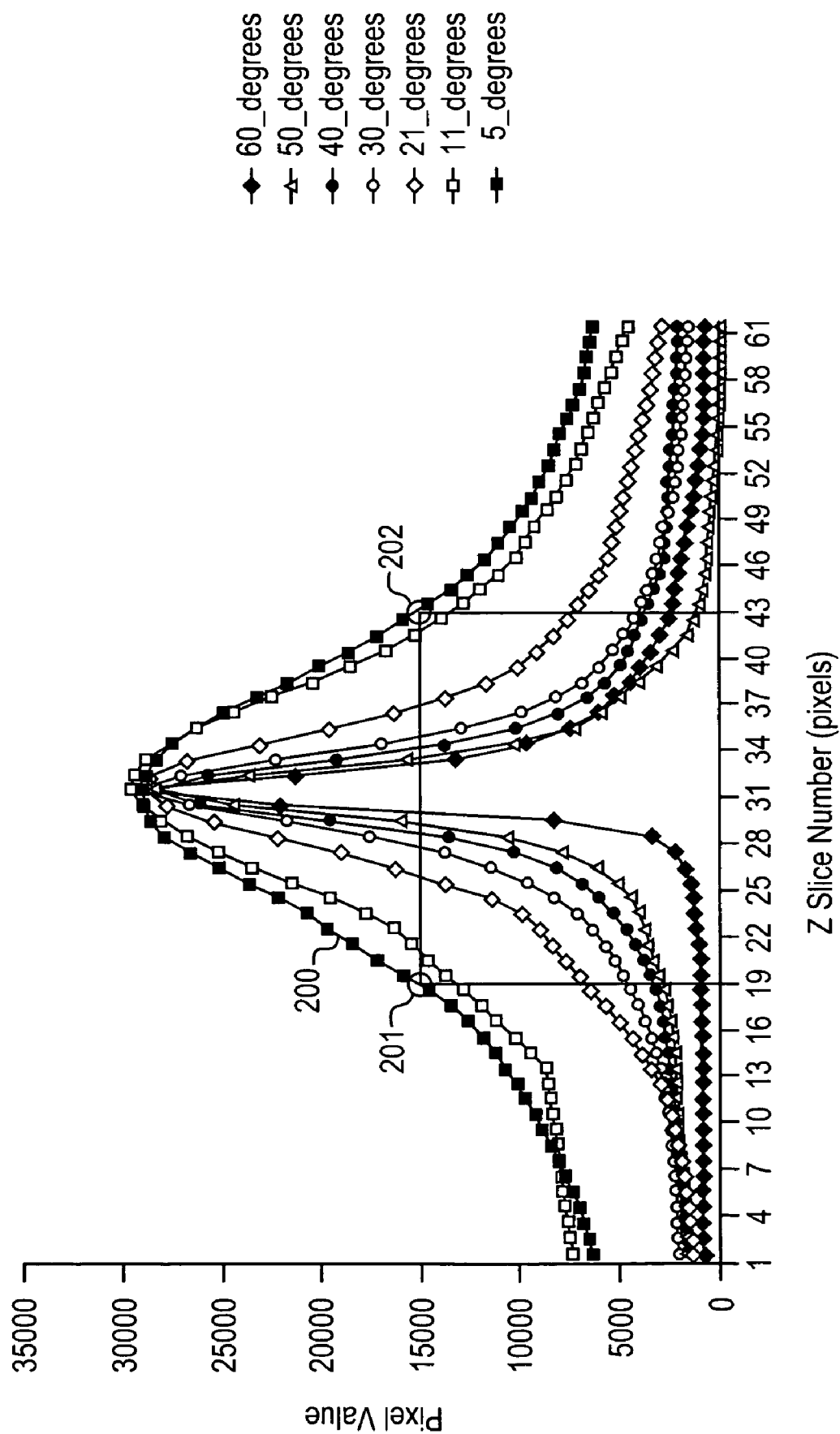
FIG. 2 depicts a graph illustrating exemplary slice sensitivity profiles for different x-ray source sweep angles in accordance with embodiments of the invention.

Referring to FIG. 2, a set of curves, each representing the different slice sensitivity profiles 130 for the corresponding sweep angle θ value of an embodiment of the invention is represented. These curves demonstrate a full width half maxima determination of the nominal slice thickness 126. The X-Axis represents a number of pixels, and the Y-Axis represents a pixel value. For example, an outermost curve 200 represents the slice sensitivity profile 130 when θ is equal to five degrees. The maximum pixel value is approximately 30,000, therefore the half maxima value is approximately 15,000. Referring to the curve 200, two points 201, 202 along the curve representing a Y-axis pixel value of approximately 15,000 are depicted. The points 201 and 202 correspond to X values of approximately 19 and 43, respectively. Therefore, the minimum (nominal) slice thickness 126 for the embodiment described by FIG. 2 in response to the sweep angle θ of 5 degrees is approximately 43 minus 19, or 24 pixels. If the pixel spacing of the detector panel 150 is known, the value for minimum slice thickness 126 can be determined. It may be appreciated from the set of curves and the graph legend of FIG. 2 that as the sweep angle θ increases, the nominal slice thickness 126 decreases. It may also be appreciated that while the minimum (nominal) slice thickness 126 is primarily determined by a physical constraint (sweep angle θ), and may not be reduced further (without increasing the sweep angle θ), there is no such physical constraint upon combining slices 121 to provide a slice 125 with greater thickness in the z-direction 127.

The selection of appropriate slice thickness is dependent upon the application requirements as well as the radiologist preference. Use of the nominal slice thickness 126 may provide the maximum sharpness, contrast, and resolution for the z-dimension 127 within a given image slice 121. However, use of image slices 125 that are thicker than the nominal slice thickness 126 provide practical benefits. As used herein, image slice 126 is referred to as a nominal slice thickness defined by sweep angle θ, while image slice 125 is referred to as a given slice thickness that may be thicker than the nominal slice thickness 126. If tomosynthesis is to be used for the detection of breast cancer for example, the objective is to detect the presence of micro calcification clusters. Although detailed evaluation of small objects, such as individual micro calcifications may be enhanced by the increased resolution of the nominal slice thickness 126, quantification of micro calcifications within the cluster and cluster size determination may be improved with the selection of an increased image slice thickness 125 to enlarge the field of view, thereby surrounding the boundaries of the cluster. In a similar way, the larger field of view provided by a thick image slice 125 enhances diagnosis of interstitial diseases. Thicker imaging slices 125 can allow visualization of the entire vessel including a potential blockage, as distinguished from image slices of nominal thickness 126, which are only able to visualize a portion of the vessel.

Figure 3B:
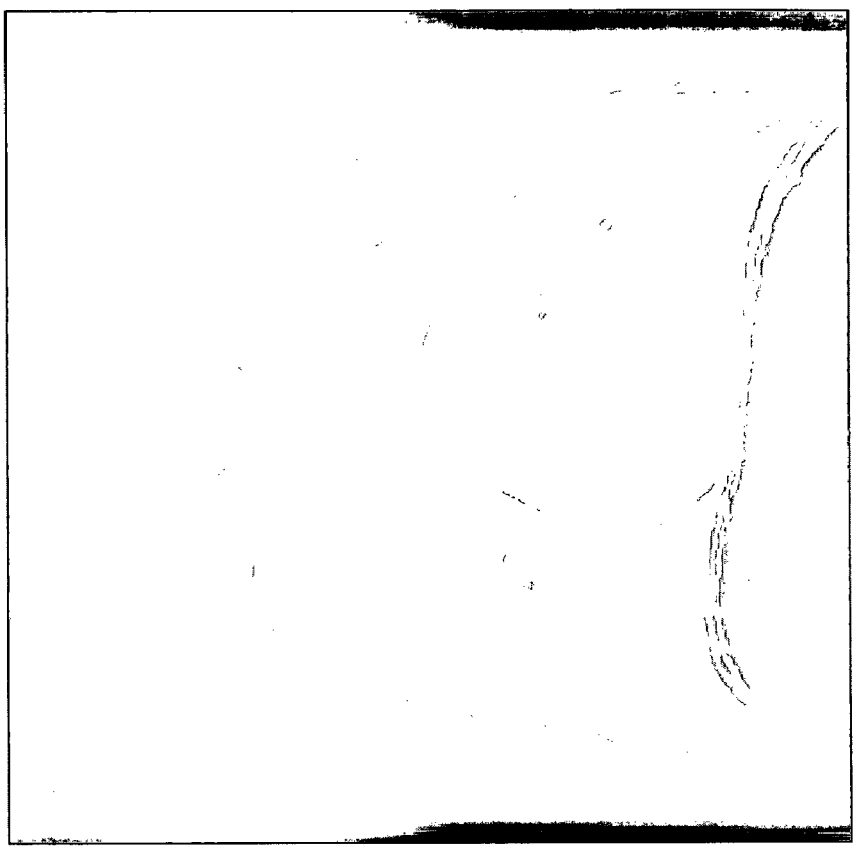
FIGS. 3A and 3B depict exemplary embodiments of two digitized images of a medical data display in accordance with embodiments of the invention.
Figure 3A:
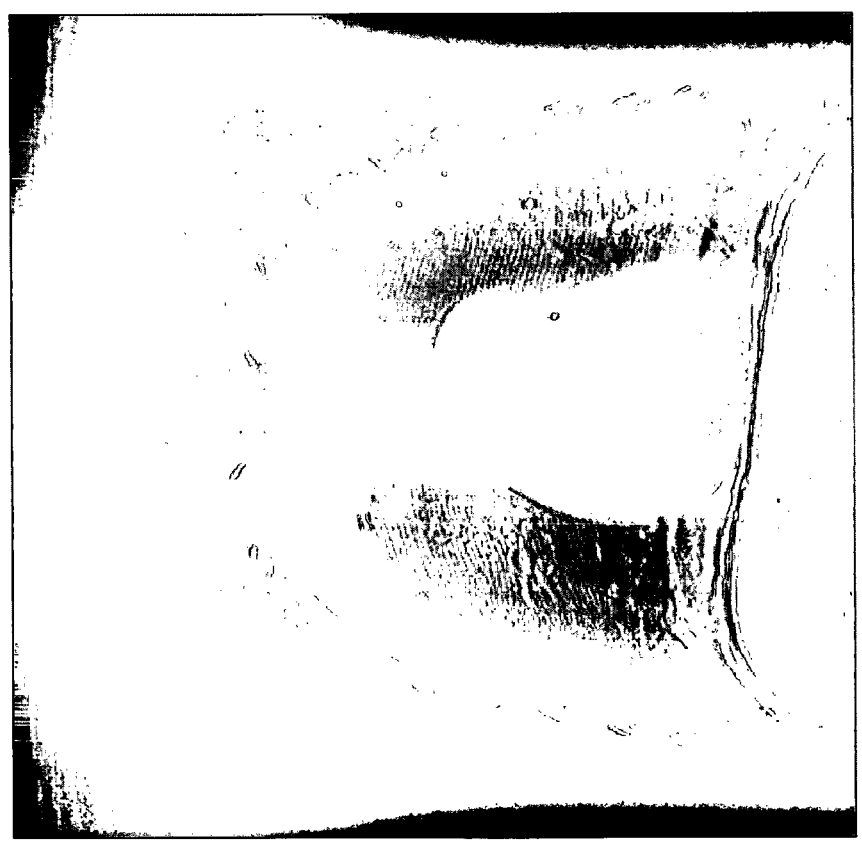

Referring now to FIGS. 3A and 3B, an image is depicted on the left (3A) that has been generated from the nominal thickness image slice 126, and an image is depicted on the right (3B) that has been generated via transformation of multiple nominal thickness image slices 126 to create one, thicker image slice 125. Use of the thicker image slice 125 will improve data consistency, resulting in the reduction of image artifacts, ringing, and a higher signal to noise ratio. These benefits may be seen by comparing the image on the left (FIG. 3A) to the image on the right (FIG. 3B).

An additional benefit to the use of thicker image slices 125 generated from multiple image slices of nominal thickness 126 relates to the workflow of the radiologist. For example, if an embodiment of the imaging object 120 has a thickness in the z-direction 127 of 10 cm, and the nominal slice thickness 126 is 1 mm, one hundred image slices having with the nominal (also herein referred to as a first) slice thickness 126 will be generated. Alternatively, if the radiologist chooses to transform the image slice to a second thicker slice thickness 125 of 1 cm, the number of image slices will be reduced from one hundred to ten, allowing the radiologist to review the condition of the imaging object 120 more quickly.

A function rule to create a second set of image slices 125 having increased thickness may be represented by the following form:

$$G_j = S_{start\_index} * W_{start\_index} + \sum_{i=start\_index+1}^{end\_index-1} S_i * W_i + S_{end\_index} * W_{end\_index} \quad \text{Equation-1}$$

where:

$G_j$ (j=0, 1, ... M) represents the second set of image slices 125 having the second (user-selected) slice thickness, $S_i$ (i=0, 1, ... N) represents a first set of image slices having the first (nominal) slice thickness 126, start_index, end_index define the first and last slices, respectively of the first set of images at the nominal slice thickness 126, $W_i$ are weighting coefficients determining the contribution from each nominal slice 126, $S_{start\_index}$ represents the first slice from the first set of image slices having the first (nominal) slice thickness 126, $W_{start\_index}$ represents the weighting coefficient determining the contribution from the first slice from the first set of image slices having the first (nominal) slice thickness 126, $S_{end\_index}$ represents the last slice from the first set of image slices having the first (nominal) slice thickness 126, $W_{end\_index}$ represents the weighting coefficient determining the contribution from the first slice from the first set of image slices having the first (nominal) slice thickness 126, and M and N are integers, and M<N.

Referring back to FIG. 1, the processing device 160 reconstructs the plurality of projection images into the first set of object image slices 126 at the nominal slice thickness. In response to the radiologist providing a set of parameters 301, 306, 311, described further below with reference to FIG. 6, via the input device 157, the processing device 160 applies the aforementioned function rule to transform the first set of image slices 126 into the second set of image slices 125 having the increased slice thickness using the preceding formula, Equation-1. Equation-1 describes a function rule utilizing a weighted summation to transform the first set of nominal thickness image slices 126 to the second set of image slices 125, having a greater thickness. As used herein, the term weighted or weighting refers to a function rule for adjusting the value of a given variable. The weighting coefficients may be a function of any form. One embodiment of a weighting function is depicted in FIG. 4, which provides greater weight (influence) to the central image slices 126 than those at the ends of the first set of image slices 126. The exemplary weighting function depicted in FIG. 4 and utilized within Equation-1 is defined such that the weighting coefficients sum to 1.0, wherein W1+W2+ ... WN=1.0. While an embodiment of the invention has been described employing a linear weighting function possessing a triangular shape to bias the central image slices 126 as depicted in FIG. 4, it will be appreciated that the scope of the invention is not so limited, and that the invention also applies to other weighting functions, such as a polynomial or exponential function, with or without a central bias, which may also be applied to projection images, for example. It will be further appreciated that while FIG. 4 may imply that the weighting function is to be applied over the entire range of projection images or of nominal thickness image slices 126, the weighting function may also be utilized over a subset of the projection images, or of the nominal thickness image slices 126.

While an embodiment of the invention has been described employing the function rule for slice thickness transformation via the weighted summation of the nominal slice thickness image slices 126, (within the image domain, following reconstruction of projection images into object images) it will be appreciated that the scope of the invention is not so limited. Additional function rules may utilize other image attributes, such as frequency components, signal strength, pixel value, brightness, or contrast, for example, to transform image slice thicknesses. For example, an alternate function rule may provide image slice 121 thickness transformations via weighted frequency band summation (also within the image domain). With weighted frequency band summation, the first set of image slices 126 are broken into discrete frequency bands, which are then weighted, summed, and transformed into the second set of thicker image slices 125. Another image slice 121 transformation method is weighted projection summation (within the projection domain), wherein the projection images acquired via the panel detector 150 are weighted, summed, and processed prior to reconstruction into the first set of image slices 126, for example.

It will be appreciated however, that there is a practical limit to the benefits provided by thicker image slices 125. As greater numbers of image slices 121 are combined, there is increased averaging, or loss, of depth information. For example, if all of the nominal thickness image slices 126 were to be transformed into a single, thick image slice 125, (assuming a perfect transformation function rule), it would provide no beneficial information beyond a two-dimensional radiographic projection image.

Figure 5:
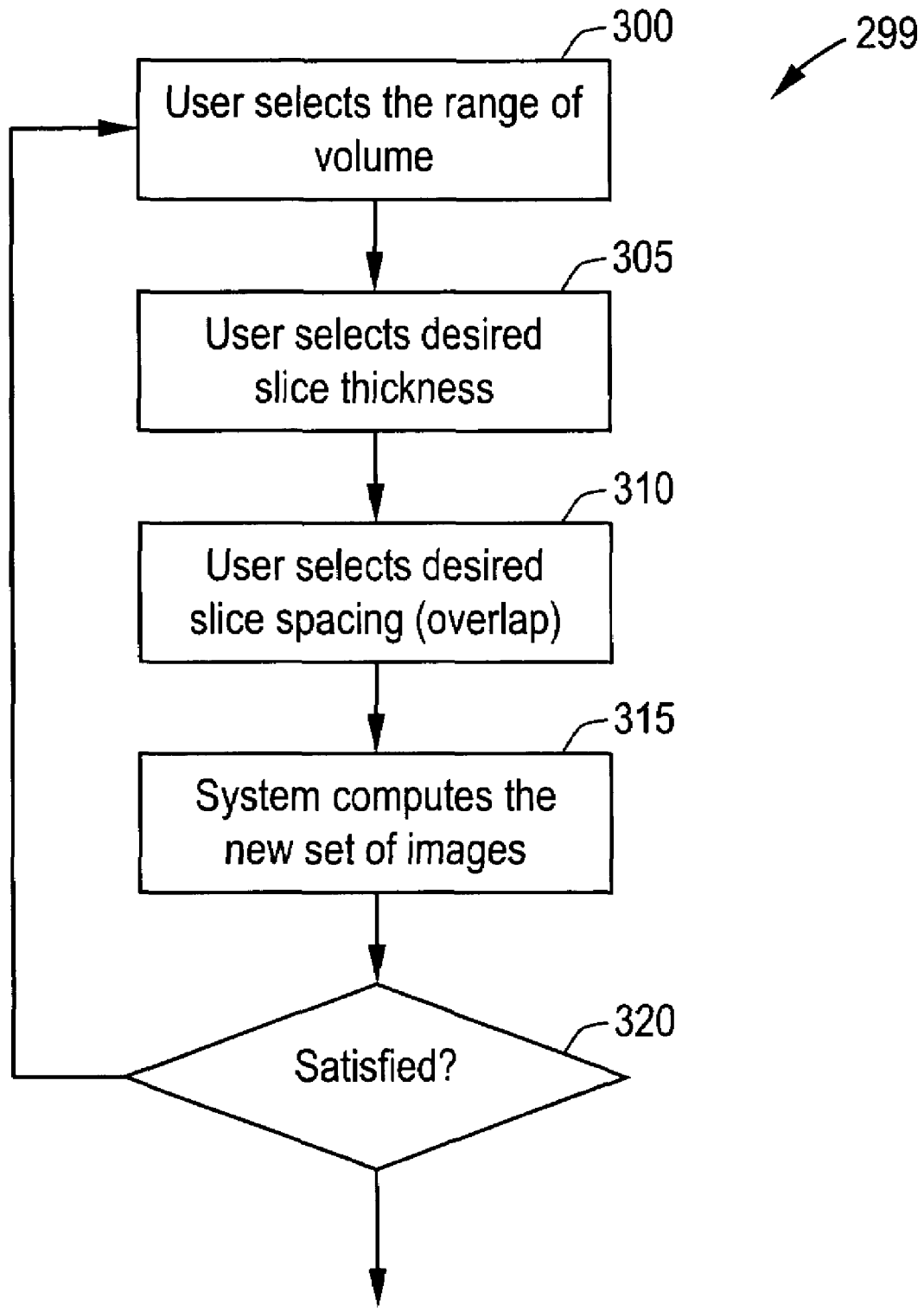
FIG. 5 depicts an exemplary embodiment of a method for optimizing the transformation of image slices in accordance with embodiments of the invention.

Referring now to FIGS. 5 and 6 collectively, an embodiment of a method 299 to optimize the selection of image slice 121 thickness by the radiologist is depicted. Block 300 represents selection of a range of a volume of interest (also herein referred to as a volume range) 301. The volume range 301 describes the dimension of the volume of interest within the imaging object 120 in the z-direction 127, and is established by selecting a start height and an end height (see FIG. 6) of the volume of interest. Block 305 represents selection of an image slice thickness 306, and block 310 represents selection of an image slice spacing (overlap) 311. Slice thickness 306 defines the dimension in the z-direction 127, as selected by the radiologist, of the image slice 125 with the second, greater thickness. Image slice spacing (overlap) 311 describes how much image information each image slice 125 having the second, user-selected thickness will share with the adjacent image slices 121. Block 315 represents transformation of the first set of nominal thickness image slices 126 to the second set of thicker imaging slices 125 by the processing system 160. Block 320 represents determination by the radiologist whether the second set of thicker image slices 125 fulfills the diagnostic objectives. If the second set of thicker image slices 125 does not fulfill the diagnostic objectives of the radiologist, the method 299 is repeated until the radiologist is satisfied with the results of the second set of thicker image slices 125.

The volume range selection 300, slice thickness selection 305, and slice spacing (overlap) selection 310 may be may be accomplished via direct input of the image parameters 301, 306, 311 into an ASCII or binary computer configuration file. However, the editing of such files required by repeated iterations of changes may become time consuming. FIG. 6 depicts an embodiment of a dialog window 419 to allow the radiologist to input the parameters 301, 306, 311. The volume range 301 may be input via a pair of dialog boxes 420, 421, the slice spacing (overlap) 311 via a dialog box 422, and the slice thickness 306 via a drop-down box 423 by the radiologist. Note that subsequent to the input of the parameters 301, 306, 311 via the dialog window 419, the radiologist must exit the dialog window 419 to view and evaluate the effects of these parameters 301, 306, 311. A significant amount of time may be required to switch between the dialog window 419 and the image if multiple iterative loops of the parameter selection 300, 305, 310 are necessary to obtain a satisfactory image for diagnostic purposes.

Figure 7:
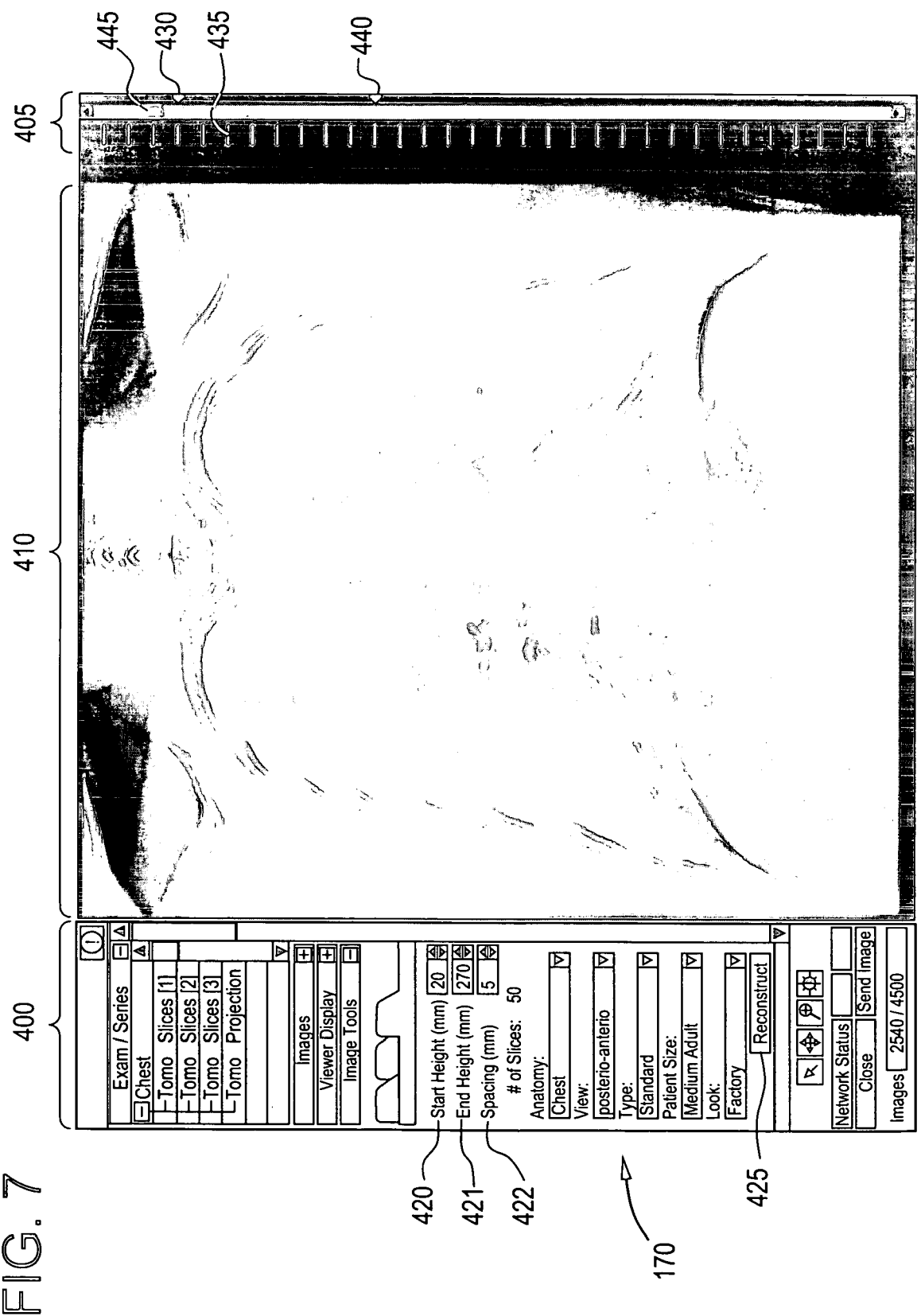
FIG. 7 depicts an exemplary embodiment of a user interface to input image parameters and simultaneously observe parameter effects on image data in accordance with embodiments of the invention.

Referring now to FIG. 7, an embodiment of a user interface for the input of the image parameters 301 (via dialog boxes 420, 421), 306, and 311 (via dialog box 422) is depicted. In the embodiment depicted, the display screen 170 has been divided into three zones. A first input area 400, a second input area 405, and an image viewing area 410 are depicted. The viewing area 410 is configured to display the image slices 121 at either the first (nominal) 126 or second (transformed) thickness 125. The first input area 400 may provide the radiologist access to a variety of image viewing and analysis tools, which will be well known to one skilled in the art. In the embodiment depicted, the first input area 400 also allows the radiologist to input the volume range 301 and slice spacing (overlap) 311 function rule parameters via the dialog boxes 420, 421, 422. A button 425 within the first input area 400 applies the function rule and parameters 301, 306, 311 to create and display an image slice 121 from the second set of image slices 125 within the image viewing area 410. The second input area 405 contains a first arrow 430, a second arrow 440, and a set of tick marks 435 arranged proximate to a slider bar 445 to represent the image slice thickness 306 and/or volume range 301. The radiologist may utilize the input device 157 to position the first arrow 430 and the second arrow 440 to represent the desired slice thickness 306 and/or volume range 301 function rule parameters.

In the embodiment of a user interface depicted in FIG. 7, it may be seen that nine tick marks 435 are depicted between the arrows 430, 440 (inclusive). This may be interpreted to indicate that the image displayed within the image viewing area 410 represents a transformed, thicker image slice 125, which has been created from eight image slices of nominal slice thickness 126. The image viewing area 410 allows the radiologist to view the effects of parameter 301, 306, 311 changes without the need to close or open any additional dialog windows 419. The image resulting from the parameters 301, 306, 311 selected by the radiologist may be reviewed in the image viewing area 410 to determine if the result is acceptable. If it is not acceptable, one of the parameters 301, 306, 311 may be changed, and the effect simultaneously observed in the image viewing area 410. By incorporating the parameter selection 300, 305, and 310, and the display image, within the same user interface of the display screen 170, the amount of discrete steps (and therefore, time) to determine the appropriate slice thickness for a specific diagnostic application may be reduced. While an embodiment has been described depicting the image viewing area 410 disposed between the first input area 400 and the second input area 405, it will it will be appreciated that the scope of the invention is not so limited, and that the invention also applies to other arrangements of the display screen 170, such as having both the first input area 400 and the second input area 405 combined into one input area located above, below, to the left of, or, to the right of the image viewing area 410, for example.

As disclosed, some embodiments of the invention may include some of the following advantages: the ability to modify image slice thickness to suit radiologist preference and the diagnostic needs of the application; the ability to reduce radiologist workflow by minimizing the total number of images for review; the ability to enhance image quality by reducing ringing, image artifacts, and increasing the signal to noise ratio; and, the ability to observe effects of slice thickness modification in a single user interface without switching between different windows.

An embodiment of the invention may be embodied in the form of computer-implemented processes and apparatuses for practicing those processes. The present invention may also be embodied in the form of a computer program product having computer program code containing instructions embodied in tangible media, such as floppy diskettes, CD-ROMs, hard drives, USB (universal serial bus) drives, or any other computer readable storage medium, wherein, when the computer program code is loaded into and executed by a computer, the computer becomes an apparatus for practicing the invention. The present invention may also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein when the computer program code is loaded into and executed by a computer, the computer becomes an apparatus for practicing the invention. When implemented on a general-purpose microprocessor, the computer program code segments configure the microprocessor to create specific logic circuits. A technical effect of the executable instructions is to provide for the display of an object utilizing a second image slice thickness that varies from a first, original slice thickness, the object having been imaged via X-ray tomography.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A method for creating a variable slice thickness, via a graphical user interface, for displaying an imaged object imaged via a tomosynthesis imaging system, the method comprising:

acquiring from a tomosynthesis imaging system a plurality of projection images from a plurality of different projection angles within a defined sweep angle;

reconstructing a plurality of object images from the plurality of projection images to define a first set of object image slices, each object image having a first slice thickness;

selecting a function rule via the graphical user interface;

applying the selected function rule and transforming the first set of object image slices, whole images or portions thereof or attributes thereof of the plurality of object images having the first slice thickness to create a second thicker object image slice and a second set of object image slices having the second slice thickness, thereby providing for the display of the object utilizing the second slice thickness that varies from the first slice thickness; and via the graphical user interface, providing for interactive adjustment of the second slice thickness by reselecting a function rule, thereby providing for repeated adjustment to obtain the second slice thickness relative to the first set of object image slices until a user is satisfied with object image results therefrom, where a resulting object image at the second thicker slice will tend to have reduced image noise and artifacts;

wherein the selected function rule and the reselected function rule are defined by weighting coefficients that specify the contribution from each of the plurality of object images comprising the first slice thickness, or from different attributes of the plurality of object images comprising the first slice thickness, to the plurality of object images having the associated second slice thickness;

wherein the selected function rule and the reselected function rule are further defined by the weighting coefficients that vary according to a linear function, a polynomial function, or an exponential function of slice position within the first set of object image slices;

wherein the weighting coefficients are centrally biased over the entire plurality of the first set of object image slices.

2. The method of claim 1, wherein:

the applying the function rule occurs subsequent to the acquiring and subsequent to the reconstructing.

3. The method of claim 1, wherein:

the function rule is in accordance with the following equation:

$$G_j = S_{start\_index} * W_{start\_index} + \sum_{i=start\_index+1}^{end\_index-1} S_i * W_i + S_{end\_index} * W_{end\_index};$$

$G_j(j=0, 1, \ldots M)$ represents the plurality of object images having the second slice thickness;

$S_i(i=0, 1, \ldots N)$ represents the plurality of projection images or the plurality of object images comprising the first slice thickness;

start_index, end_index define the first and last slices, respectively, of the plurality of projection images, or of the plurality of object images comprising the first slice thickness;

$W_i$ are weighting coefficients that specify the contribution from each slice of the plurality of projection images, or from each slice of the plurality of object images comprising the first slice thickness, to the plurality of object images having the second slice thickness;

$S_{start\_index}$ represents the first slice of the plurality of projection images, or of the plurality of object images comprising the first slice thickness;

$W_{start\_index}$ represents the weighting coefficient specifying the contribution from the first slice of the plurality of projection images, or of the plurality of object images comprising the first slice thickness, to the plurality of object images having the second slice thickness;

$S_{end\_index}$ represents the last slice of the plurality of projection images, or of the plurality of object images comprising the first slice thickness;

$W_{end\_index}$ represents the weighting coefficient specifying the contribution from the last slice of the plurality of projection images, or of the plurality of object images comprising the first slice thickness, to the plurality of object images having the second slice thickness;

M and N are integers; and

M is less than N.

4. The method of claim 1, wherein:

the plurality of projection images comprises radiographic images.

5. The method of claim 1, wherein the acquiring comprises:

acquiring the plurality of projection images using a stationary, flat panel, 2D detector.

6. The method of claim 1, wherein:

the first slice thickness has a minimum value that varies as a function of the sweep angle.

7. A program storage device readable by a machine, the device embodying a program or instructions executable by the machine to perform the method of claim 1.

8. The method of claim 1, wherein:

the weighting coefficients sum to 1.

9. The method of claim 1, wherein:

the function rule is symmetrical about a center slice of the first set of object image slices.

* * * * *